United States Patent [19]

Gloyer et al.

[11] 3,932,521

[45] Jan. 13, 1976

[54] PROCESS FOR MANUFACTURE OF KETONES FROM OLEFINS

[75] Inventors: Stewart E. Gloyer, Arlington Heights, Ill.; Lawrence A. Fury, Memphis, Tenn.

[73] Assignee: Kraftco Corporation, Glenview, Ill.

[22] Filed: Mar. 8, 1974

[21] Appl. No.: 449,328

Related U.S. Application Data

[63] Continuation-in-part of Ser. No. 113,627, Feb. 8, 1971, abandoned.

[52] U.S. Cl. ...... 260/597 B; 260/604 R; 260/533 R
[51] Int. Cl.$^2$ .......................................... C07C 45/04
[58] Field of Search ................................. 260/597 B

[56] References Cited
UNITED STATES PATENTS

3,365,499    1/1968    Clement et al. ................. 260/597 B

FOREIGN PATENTS OR APPLICATIONS

2,205,899    8/1972    Germany

OTHER PUBLICATIONS

Clement et al., J. Org. Chem., Vol. 29, pp. 241–243.

*Primary Examiner*—James O. Thomas, Jr.
*Assistant Examiner*—James H. Reamer
*Attorney, Agent, or Firm*—Fitch, Even, Tabin & Luedeka

[57] ABSTRACT

A carbonyl compound is prepared from an unsaturated olefin charge stock having at least five carbon atoms per molecule. In the process, a reaction mixture is provided including the charge stock, a catalyst system, a high boiling solvent and a polar solvent. The resulting mixture is then treated to effect a substantial conversion of the unsaturated olefin hydrocarbon to a carbonyl compound. Thereafter, a reaction product including the carbonyl compound is separated from the catalyst system and other components of the reaction mixture by distillation.

5 Claims, No Drawings

PROCESS FOR MANUFACTURE OF KETONES FROM OLEFINS

The present application is a continuation-in-part of U.S. Pat. application Ser. No. 113,627, filed Feb. 8, 1971, now abandoned.

The present invention relates generally to the preparation of carbonyl compounds by the oxidation of unsaturated liquid olefin compounds and, more particularly, the present invention relates to the recovery of the platinum group metal catalyst used in the oxidation reaction.

It is known to prepare acetaldehyde from ethylene by a process wherein ethylene is contacted with an oxygen containing gas in the presence of a compound of a metal of the platinum group and an oxidizing agent having an oxidation potential higher than that of the platinum group metal. This process is usually referred to as the "Consortium" or "Wacker" process. The Consortium process is generally applicable to the lower molecular weight olefins, such as ethylene and propylene, wherein the carbonyl compounds produced leave the reaction zone in the gaseous phase. Thus, for the lower molecular weight unsaturated olefin charge stocks, the separation of the carbonyl reaction compounds from the reaction catalyst is an easy matter. When the unsaturated olefin charge stock contains olefins having five or more carbon atoms per molecule, the olefin charge stock and carbonyl product are in the liquid phase at atmospheric pressure and ambient temperature. After the olefin charge stock is reacted to form a carbonyl product, a two-phase system is usually present with the carbonyl product in one phase and a portion of the platinum group metal catalyst and any solvents used in the reaction present in the other phase. Separation of the carbonyl product is usually made by decantation of the carbonyl product phase from the solvent phase. However, a portion of the platinum group metal catalyst is removed in the carbonyl product phase and it is difficult to recover substantially all of the catalyst from the carbonyl product phase. Due to its expense, it is important in achieving a commercially acceptable process to recover and re-use even small amounts of the platinum group metal catalyst used in effecting the reaction of the unsaturated olefin to carbonyl compounds.

Various methods have been used in an attempt to recover substantially all of the platinum group metal catalyst from the reaction product. These methods include distillation of the decanted reaction product, extraction with dimethyl sulfoxide and aqueous hydrochloric acid and contacting the carbonyl reaction product with a solid inert material at an elevated temperature for a time sufficient to precipitate the platinum group metal as the free metal on the solid inert material. None of the methods proposed for recovering the platinum group metal catalyst have been wholly successful, in that they either do not recover substantially all of the platinum group metal catalyst or they are so complex as to be economically unfeasible.

Accordingly, it is the principal object of the present invention to provide an improved process for preparing carbonyl compounds. It is another object of the present invention to provide a process for preparing a reaction product, including carbonyl compounds, wherein the reaction product is substantially free of any platinum group metal compound used as a catalyst in preparing the reaction product. It is a further object of the present invention to provide a method for utilizing a platinum group metal compound as a catalyst in a reaction and recovering substantially all of the platinum group metal catalyst for re-use.

Generally, in a process including various features of the invention, a carbonyl compound is prepared from an unsaturated olefin hydrocarbon charge stock having at least five carbon atoms per molecule by a process which comprises providing a reaction mixture including the charge stock, a catalyst system, a high boiling solvent and a polar solvent. The reaction mixture is then treated to effect a substantial conversion of the unsaturated olefin hydrocarbon to a carbonyl compound. Thereafter a reaction product, including the carbonyl compound, is separated from the catalyst system and other components of the reaction mixture by distillation.

The high boiling solvent of the invention can be any organic compound or mixture of organic compounds that is liquid under the conditions of the reaction, which has a boiling point which is a predetermined level higher than the boiling point of the carbonyl containing compound formed by the reaction, and which is a solvent for the catalyst system used in the reaction. Solvents must be selected that do not enter into the reaction and do not interfere with the reaction product. The suitability of any organic compound or mixture of organic compounds for use as a solvent in the reaction is readily determined by one skilled in the art by reference to the characteristics set forth above and which are described in more detail hereinafter.

The preferred high boiling solvents are those which have a boiling point of at least 170°C. Particularly preferred solvents are organic alcohols, acids, and nitriles which have a boiling point within the range of from about 170°C to about 320°C. The solvents may be multi-functional, that is, they may contain more than one functional group, such as hydroxyl or carboxyl groups, and may contain a combination of functional groups. Suitable solvents include, but are not limited to, diethylene glycol, 1,5-pentanediol, 1-decanol, 1-nonanol, 1-dodecanol, tetrahydrofurfuryl alcohol, hexylene glycol, glycerol, paracresol, 1,4-butanediol, benzonitrile, hexaonic acid, octanoic acid, decanoic acid, polyoxypropylene diols having an average molecular weight of up to about 600, preferred examples of which include dipropylene glycol and a polypropylene glycol having an average molecular weight of about 430, and mixtures thereof.

The high boiling solvent preferably has a boiling point at least 5°C higher than the carbonyl compound produced during the reaction. A particular high boiling solvent having the preferred boiling point may be selected from suitable high boiling solvents described above.

It has been found that the use of a polar solvent in combination with the high boiling solvent provides a reaction medium with increased reactivity. This enables the reaction to proceed at a faster rate and also provides for a more complete reaction of the olefin charge stock to the carbonyl compound. Suitable polar solvents are methanol, ethanol, propanol, isopropanol, n-butanol, sec.-butanol and dimethylformamide. The polar solvent is present at a level of from about 20 to about 60 percent by weight based on the weight of the high boiling solvent used.

The process of the invention is limited to conversion of unsaturated olefinic compounds of at least five carbon atoms, but having 20 carbon atoms or less. Those unsaturated olefinic compounds having more than 20 carbon atoms have boiling points which are excessively high and distillation to separate carbonyl compounds from the high boiling solvent must be carried out at temperatures such that charring and deterioration of the catalyst system and product are incurred. The charge stock can be any unsaturated olefinic compound having at least five carbon atoms per molecule up to 20 carbon atoms per molecule and which has at least one hydrogen atom on each carbon atom of at least one olefinic double bond. The charge stocks may have from between one and four olefinic double bonds. Mixtures of unsaturated olefinic compounds can also be used. Suitable mixtures of unsaturated olefinic compounds are olefins obtained from the thermal cracking of wax and from the polymerization of ethylene.

The products from the reaction are carbonyl-containing compounds which include ketones, aldehydes and organic acids. The principal product is the ketone and if an alpha olefin is utilized as the charge stock, a methyl ketone is almost exclusively the product obtained.

The process of the present invention is carried out with a catalyst system which includes a platinum group metal compound and which includes an oxidizing agent which has an oxidation potential higher than that of the platinum group metal compound employed. The platinum group metal compound is selected from compounds of a noble metal of Group VIII of the Periodic Table, wich includes metals such as ruthenium, rhodium, palladium, osmium, iridium and platinum. The preferred metal compounds are those of palladium and platinum. It is still more preferred to use the water-soluble salts of palladium and platinum, such as halides, sulfates or phosphates. The most preferred platinum group metal compounds are palladium chloride and platinum chloride.

Other suitable specific examples of platinum group metal compounds which may be used in the process of the invention are platinum sulfate, palladium acetate and palladium sulfate. The amount of the platinum group metal compound used in the reaction is usually from between 0.01 and 20 weight percent based on the weight of the high boiling solvent which is used. The preferred amount is from between about 0.5 and 5 weight percent of the platinum group metal compound.

In the process the platinum group metal compound is reduced while promoting the oxidation of the olefin by forming a complex with the unsaturated charge stock which then decomposes to form a reduced platinum group metal compound and the carbonyl compound. The reduced platinum group metal compound is inactive to promote further oxidation until it is again in a proper oxidation state. The catalyst system also includes an oxidizing agent which, while not reacting with the unsaturated charge stock, the high boiling solvent or the reaction products, is capable of oxidizing the platinum group metal compound to an active state. Thus, the platinum group metal compound can be used in stoichiometric quantities to produce the desired carbonyl compounds, but in order for the platinum group metal to function as a catalyst and not as a reactant, it must be reoxidized to the proper valence state. In view of the expense of the platinum group metal compounds, the reoxidation of the platinum group metal compound is the only practical means of operating the process.

It would be desirable, of course, to reoxidize the platinum group metal with an oxidizing gas, such as oxygen, but this reaction does not occur readily. It has been found that certain organic compounds, for example the quinones, are suitable oxidizing agents. Other organic oxidizing agents can also be employed, such as the organic peroxides, organic halamides, organic halimides and organic hypohalites.

Inorganic oxidizing agents can also be used. These include compounds such as ozone, hydrogen peroxide, sodium peroxide or compounds of the higher valence state of metals such as copper, iron, cobalt, nickel, manganese, chromium, lead, vanadium and others.

The organic oxidizing agents and many of the inorganic oxidizing agents are equally difficult to reoxidize with an oxygencontaining gas. It is consequently preferred to employ a redox system comprising an oxidizing agent which has an oxidation potential higher than that of the platinum group metal compound and an oxygen containing gas, said oxidizing agent being such that it is itself reoxidized with a oxygen containing gas. A class of compounds which are suitable for use in a redox system include the compounds of copper, iron, cobalt, manganese and nickel. Particularly preferred are the halide derivatives of copper, and most preferred is copper chloride.

The amount or concentration of the oxidizing agent will vary depending, in part, on whether it is employed alone or as part of a redox system. In the case where the oxidizing agent is employed alone, such as where a quinone is used, the amount of oxidizing agent can vary between 1 and 50 weight percent of the total reaction mixture with preferred amounts between 5 and 25 weight percent.

Where a redox system is employed, the molar ratio of the sum of the redox metals to the platinum group metal is at least 1:10 and preferably between 1:1 and 100:1.

Water must also be present in the reaction system but need be present only in trace amounts. The function of the water is to provide the necessary oxygen to form the desired carbonyl compound from the decomposition of the platinum group metal compound-olefin complex. In general, the amount of water can vary between about 0.05 and about 20 weight percent based on the high boiling solvent with preferred concentrations being between about 0.5 and about 17 weight percent. The most preferred concentrations will depend in part on the high-boiling solvent employed. For example, when 1,5-pentanediol is employed as the solvent, the preferred water concentration is between 0.2 and 7 weight percent. Too high a water concentration results in poor olefin solubility with consequent low conversion levels.

In general, the olefin charge stock can be added to the reaction system at a level of from about 0.5 to about 1200 percent by weight of the high boiling solvent. For batch and semi-batch reactions, it is preferred that the olefin charge stock be added at levels of from about 40 percent to about 600 percent by weight of the high boiling solvent.

When a redox system is employed which utilized an oxygen-containing gas to reoxidize a redox metal, then any oxygen-containing gas can suitably be employed, for example, air, oxygen, oxygen-enriched air, or air or oxygen diluted with an inert gas, such as nitrogen. The rate of addition of the oxygencontaining gas will depend, of course, on the oxygen content, but in general should be such as to substantially completely react while in the reaction zone. The preferred oxygen-containing gases are those having an oxygen content between 5 and 100 weight percent.

The process of the invention is adapted to batch, semibatch and continuous manufacture of carbonyl compounds. In this connection, known process conditions for effecting the reaction of unsaturated olefinic hydrocarbons to carbonyl containing compounds may be used in the invention. The reaction may be effected at various pressures and temperatures in accordance with known conditions. A process is known for reacting unsaturated olefinic compounds to provide carbonyl-containing compounds wherein an unsaturated olefinic charge stock is added continuously to a reaction mixture. The reaction mixture includes a compound of a metal of the platinum group, an oxidizing agent having an oxidation potential higher than that of the platinum group metal and a low boiling solvent. The charge stock is added continuously at a rate equivalent to the rate of reaction of the charge stock to the carbonyl containing compound.

After the reaction of the unsaturated olefin compound to a carbonyl-containing compound has been effected, the distillation step of the present invention is used to separate a reaction product containing the carbonyl compound from the reaction mixture. The distillation step may be conducted under vacuum, atmospheric or super-atmospheric conditions. In this connection, the temperature of the cooling fluid used to condense the reaction product is adjusted, based upon the conditions under which the distillation is effected. In general it is desirable to provide the condensing fluid at a temperature at least 20°C below the boiling point of the lowest boiling component of the reaction mixture.

It is preferred not to use pressure conditions during distillation of the product from the high boiling solvent that result in a temperature of distillation that is so high as to damage the carbonyl product or the high boiling solvent. In this connection it is preferred that the distillation be effected at a temperature of from about 5°C to about 150°C. The temperature of distillation may be regulated by adjusting the pressure during the distillation. In this connection, the preferred pressure during distillation is an absolute pressure within the range of from about 5 microns to atmospheric. It is particularly preferred to use reduced pressures of from about 5 microns to about 100 mm Hg. and to effect the distillation by flash evaporation and steam stripping.

After the distillation step, the catalyst system remains within the distillation chamber, and may be re-used. The high boiling solvent, which also remains substantially within the distillation chamber, may also be re-used so long as the temperature at which the distillation is effected is not sufficient to damage the high boiling solvent. The liquid reaction product obtained by distillation containing the carbonyl compound may be further treated by fractional distillation to separate the polar solvent from the carbonyl containing compound and to recover a pure carbonyl-containing compound. The catalyst system is usually present in the liquid reaction product in amounts of less than about 25 parts per million.

The following examples further illustrate various features of the invention, but are intended to in no way limit the scope of the invention which is defined in the appended claims.

EXAMPLE I

The six-carbon olefin, 1-hexene is introduced to a reaction mixture having a catalyst system and is reacted to provide the ketone 2-hexanone. The method of the invention is then used to recover the catalyst system used in effecting the reaction.

A reaction flask is fitted with a mechanical stirrer, a dropping funnel, a thermometer, a gas dispersion tube and a condensing system. The gas dispersion tube is fitted so as to extend to the bottom of the reaction flask so that the reaction mixture covers the outlet of the gas dispersion tube. The condenser system is used to condense volatile reaction components during the reaction process and to reflux the condensed reaction components into the reaction flask.

A catalyst solution is prepared by dissolving 0.04 mols of palladium chloride, and 0.3 mols of cupric chloride in a mixture of 126 grams of 1,5-pentanediol, 68.5 grams of methanol, and 21.4 grams of water. The catalyst solution is added to the reaction flask described above and is heated to a temperature of 38°C and maintained at that temperature throughout the reaction. Oxygen is admitted into the reaction flask through the gas dispersion tube, and an oxygen flow rate of 0.5 liters per minute is initiated and maintained. 50.4 grams of 1-hexene is added to the catalyst solution all at once. After the 1-hexene is added to the catalyst solution, the reaction mixture is stirred for 1.5 hours with the temperature maintained at 38°C.

The reaction mixture is then vacuum distilled at an absolute pressure of 2-4 mm Hg pressure until a temperature of about 30°C is reached. The distillate is collected and analyzed by gas liquid chromotography (GLC). The yield of 2-hexanone is 48 percent, based on the level of 1-hexene, which is charged to the reaction flask. The distillate contains less than 25 ppm of the catalyst system.

EXAMPLE II

The apparatus described in Example I is used to prepare 2-pentanone from 1-pentene. A catalyst solution is prepared by dissolving 0.04 mols of palladium and 0.3 mols of cupric chloride in a mixture of 126 grams of diethylene glycol, 68.5 grams of methanol and 21.4 grams of water. The catalyst solution is transferred to the reaction flask and is heated to a temperature of 28°C. An oxygen flow of 0.5 liters per minute is established throught the catalyst solution. 49 grams of 1-pentene is added by means of the dropping tube to the catalyst solution over a period of 6 hours.

The reaction mixture is then transferred to a distillation flask and is vacuum distilled at a pressure of 2–4 mm. of mercury absolute pressure until a temperature of 30°C is reached. The distillate is collected and analyzed and it is found that 34 percent by weight of the 1-pentene charge has been converted to 2 pentanone. The combined level of copper and palladium in the distillate is less than 25 ppm.

EXAMPLE III

The method of the present invention is used to convert 1-hexene to 2-hexanone under pressure conditions. A catalyst solution containing 126 gm. diethylene glycol, 68.5 gms. methanol, 7.12 gms. palladium chloride and 41 gms. copper chloride is charged to a 2 liter autoclave. The autoclave is purged with oxygen and the catalyst solution is heated to the reaction temperature of 50°C. The autoclave is then pressurized with oxygen to a pressure of 100 psig. 100.8 grams of 1-hexene is then charged to the autoclave over a period of 10 min. by means of a metering pump. Throughout the reaction, the catalyst solution is stirred at 1,000 r.p.m. and the temperature is maintained by cooling. The oxygen pressure is also maintained at 100 psig. throughout the reaction by re-pressurization with oxygen.

Following the completion of the 1-hexene addition, the reaction is stirred for an additional 0.5 hours.

Thereafter, the reaction mixture is transferred to a distillation flask. The mixture is then vacuum distilled at a pressure of 2–4 mm of mercury absolute pressure. The distillate was analyzed and it is found that 93 percent by weight of the 1-hexene that has been charged is recovered as 2-hexanone. The level of copper in the distillate is 6 ppm, and the level of palladium in the distillate is 2.5 ppm.

EXAMPLE IV 2-dodecanone is prepared from 1-dodecene according to the process of the present invention as follows: A catalyst solution is prepared by dissolving .04 moles of palladium chloride in a mixture of 137 grams of methanol, 252 grams of polypropylene glycol having an average molecular weight of 430, and 15 grams of water. The catalyst solution is then charged to a 2 liter titanium autoclave where the catalyst solution is heated to a temperature of 60°C; while being stirred at 1,000 r.p.m. with the reactor being pressurized to 100 p.s.i.g. with oxygen. Using a piston pump, 600 grams of 1-dodecene is introduced to the autoclave over a period of 2½ hours. During this period of addition, the reaction temperature is maintained at 60°C by cooling, with the reaction pressure of 100 p.s.i.g. being maintained by repressurization with oxygen. Stirring is continued for about ½ hour after the addition of 1-dodecene is completed.

The crude reaction mixture is then steam stripped at a vacuum of 29 inches, gauge until a temperature of 100°C is achieved. The distillate is then collected and analyzed by gas liquid chromotography (GLC). The yield of 2-dodecanone is 93% based on the level of 1-dodecene which is charged to the autoclave. The distillate contains less than 25 ppm of the inorganics of the catalyst system.

Utilizing the apparatus and catalyst solution described in Example IV above and under substantially identical conditions set forth therein, 600 grams of 1-tetradecene is reacted such that an 88% yield of 2-tetradecanone is obtained, based on the level of 1-tetradecene which is charged to the autoclave. The distillate contains less than 25 ppm of the inorganics of the catalyst system.

What is claimed is:

1. In a process for preparing a reaction product including ketone compounds from a reaction mixture comprising water, an unsaturated hydrocarbon having from five to 20 carbon atoms per molecule wherein the unsaturation in said hydrocarbon resides solely in from one to four olefin double bounds and wherein there is at least one hydrogen atom on each carbon atom of at least one of said olefin double bonds, a catalyst comprising a water soluble salt of a metal of the platinum group, and an oxidizing agent having oxidizing potential higher than that of the platinum group metal salt, the improvement comprising including in said reaction mixture a polar solvent and a high boiling solvent, said polar solvent being selected from the group consisting of methanol, ethanol, propanol, n. butanol, sec. butanol, dimethylformamide and mixtures thereof, said high boiling solvent being selected from diethylene glycol, 1,5-pentanediol, 1-decanol, 1-nonanol, 1-dodecanol tetrahydrofurfuryl alcohol, hexylene glycol, glycerol, peracresol, 1,4-butanediol, dipropylene glycol, benzonitrile, hexanoic acid, octanoic acid, decanoic acid, polyropylene glycol, and mixtures thereof, said polar solvent being present in said reaction mixture at a level of from about 20 percent to about 60 percent by weight of said high boiling solvent, said unsaturated hydrocarbon being present in said reaction mixture at a level of from about 0.5 to about 1200 percent by weight of said high boiling solvent, effecting a substantial conversion of said unsaturated hydrocarbon to a ketone compound in the presence of an oxygen containing gas and separating a reaction product including said ketone compound from said platinum group metal salt and said high boiling solvent by distillation.

2. A process in accordance with claim 1 wherein said polar solvent is methanol.

3. A process in accordance with claim 2 wherein said high boiling solvent is polypropylene glycol.

4. A process in accordance with claim 2 wherein said high boiling solvent is diethylene glycol.

5. A process in accordance with claim 2 wherein said high boiling solvent is 1,5-pentanediol.

* * * * *